United States Patent [19]
Paradis

[11] Patent Number: 5,453,097
[45] Date of Patent: Sep. 26, 1995

[54] CONTROL OF FLUID FLOW

[76] Inventor: Joseph R. Paradis, P.O. Box 22238, Hilton Head Island, S.C. 29925

[21] Appl. No.: 290,133

[22] Filed: Aug. 15, 1994

[51] Int. Cl.$^6$ ................................ A61M 5/00
[52] U.S. Cl. ................... 604/247; 604/246; 604/256; 604/86; 137/849
[58] Field of Search ............... 137/512.4, 843, 137/846, 847, 848, 849, 850, 852, 854, 855; 604/30, 9, 81, 80, 86, 905, 91, 246, 247, 245, 256, 323, 326, 167

[56] References Cited

U.S. PATENT DOCUMENTS

| | | | |
|---|---|---|---|
| 236,719 | 1/1881 | Renton | 137/849 |
| 2,670,757 | 3/1954 | Delany | 137/849 |
| 4,133,457 | 1/1979 | Klassen | 137/849 |
| 4,141,379 | 2/1979 | Manske | 604/246 |
| 4,143,853 | 3/1979 | Abramson | 604/246 |
| 4,222,407 | 9/1980 | Ruschke et al. | 137/855 |
| 4,387,879 | 6/1983 | Tauschinski | 137/846 |
| 4,556,086 | 12/1985 | Raines | 137/843 |
| 4,610,276 | 9/1986 | Paradis et al. | 604/86 |
| 4,620,648 | 11/1986 | Schwartzman | 137/849 |
| 4,683,916 | 8/1987 | Raines | 604/247 |
| 4,762,149 | 8/1988 | Pickl, Jr. | 137/843 |
| 4,798,594 | 1/1989 | Hillstead | 604/256 |
| 4,946,448 | 8/1990 | Richmond | 604/247 |
| 5,009,391 | 4/1991 | Steigerwald | 137/849 |

Primary Examiner—C. Fred Rosenbaum
Assistant Examiner—N. Kent Gring
Attorney, Agent, or Firm—George E. Kersey

[57] ABSTRACT

Valve apparatus and method with an elastomeric disk fixedly disposed between inlet and outlet members and being deformable to permit flow through the inlet to the outlet. Deformation of the disk in the direction of pressure through the outlet is limited. The elastomeric disk can be circular with a linear or non-linear slit and be clamped between the inlet and outlet members. The structure for limiting disk deformation can take the form of a pilot integrated into, and extending across, the inlet member in centrally or non-centrally apertured form.

19 Claims, 9 Drawing Sheets

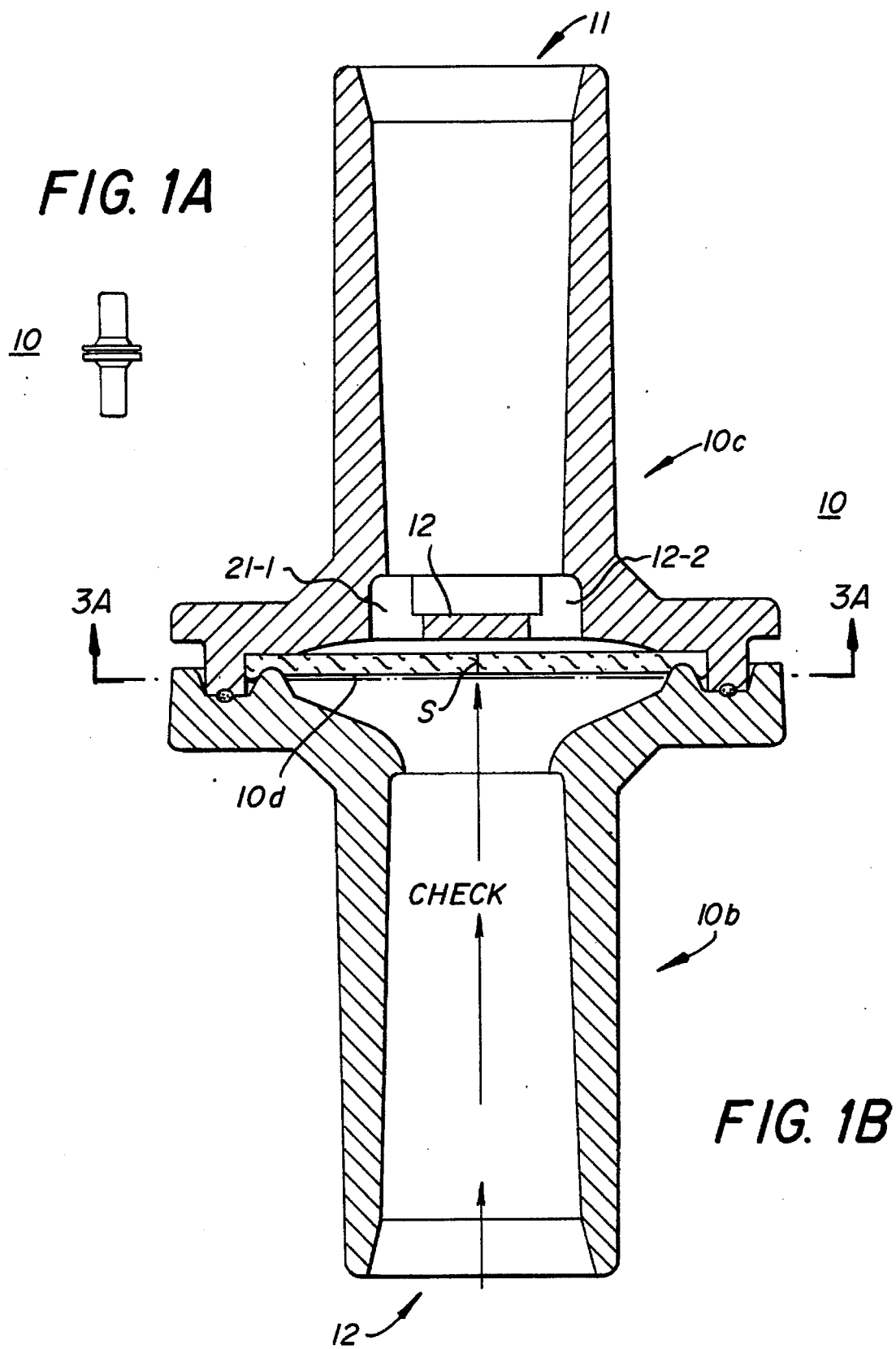

FIG. 7B
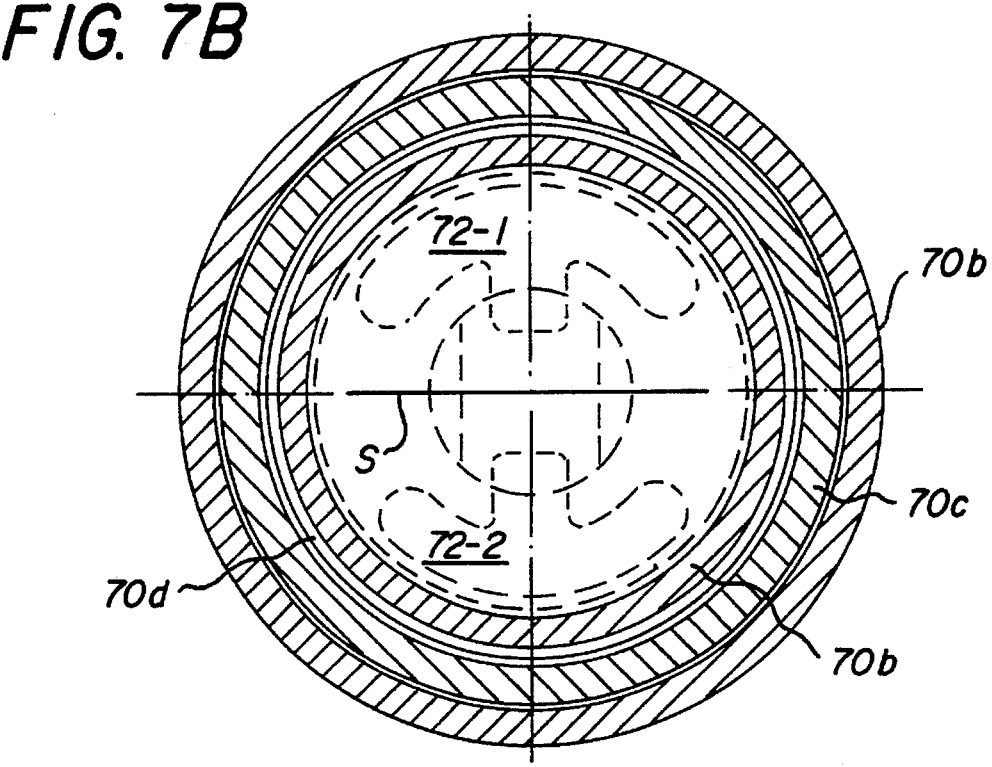
FIG. 7C
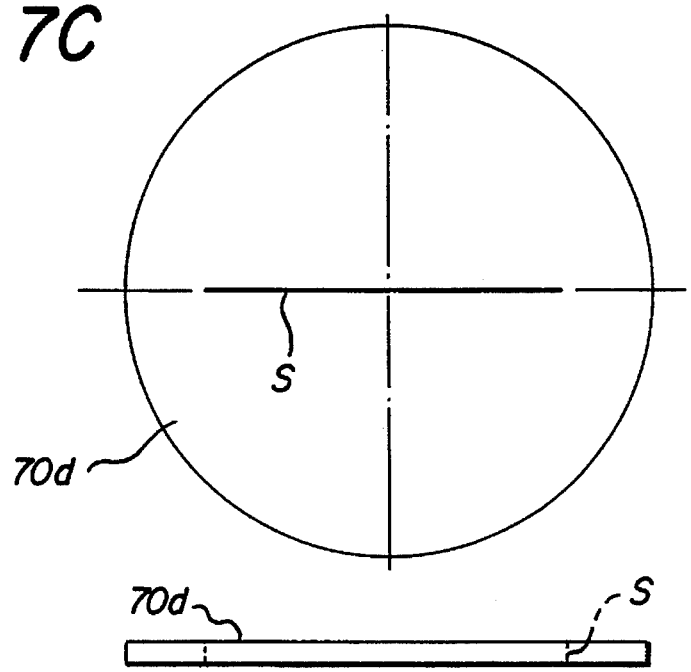
FIG. 7D

CONTROL OF FLUID FLOW

This invention relates to the control of fluid flow between an inlet and an outlet and more particularly to flow control by a plastic valve which is adapted for use in IV (intravenous) systems to "check" flow, by preventing backflow, or for connection to a cannula or catheter by which a parenteral (body-entrant) solution or medication is applied to a patient.

BACKGROUND OF THE INVENTION

Parenteral solutions, including fluids and blood products, or medications, often need to be applied to patients. Entry into the patient is through a cannula (blunt needle-like tube) or catheter (flexible tube), which often contains a sharp metallic or non-metallic needle for piercing skin and tissue. Once the piercing has taken place, and the cannula or catheter fixed in position, the needle can be withdrawn, and the catheter or cannula connected to other components by which fluids are introduced for therapy or diagnosis.

When a vein is to be entered, it is squeezed on its distal side to produce swelling and facilitate puncturing by a cannula or catheter contained needle, which is then removed from its cannula or catheter holder. After puncturing, it is virtually impossible to prevent an emergence of fluid, because of blood pressure, from the valve connected to the cannula. If, for example, a short catheter is introduced into a large venacava, and subsequently advanced to the venacava superior, a significant emergence of fluid cannot be prevented. In this case, an improperly placed patient, or one who makes spontaneous movements, is subject to the danger that a vacuum may occur in the punctured venacava so that air is sucked through the catheter resulting in air embolism.

In an attempt to limit the deficiencies of the prior art, U.S. Pat. No. 4,387,879 "Self-Sealing Connector for Use with Plastic Cannulas and Vessel Catheters" issued Jun. 14, 1983 to Stefan Tauschinski of Vienna, Austria discloses a connector that purports to insure that a metal cannula or vessel catheter can be pushed through the connector without obstruction, with the connector closing automatically as soon as the cannula or catheter has been disengaged. For that purpose, the connector is provided with an elastomeric disk having a central slit adjoining a slideable cylindrical member with tabs that slide within axial guide grooves of the housing. This construction is complex and costly to manufacture.

Other prior art disclosing devices with disks having central slits also are characterized by undue complexity. Thus U.S. Pat. No. 962,027 which issued to G. L. Kennedy, Jun. 21, 1910 for "Filler for Siphon Bottles" discloses a casing with a supply tube secured to one end, and a cap having an inwardly converging mouth closing the other end. A rubber gland is secured between the casing and cap, and a check valve within the casing has a hollow central conoidal portion slotted through its apex, a filling tube within the casing open at both ends, a disk secured to the tube, and a spring arranged to press the disk against the gland, with the other end of the tube extending into the hollow conoidal portion of the valve.

Another slotted-disk device characterized by undue complexity is in U.S. Pat. No. 3,570,484, issued Mar. 16, 1971 for "Intravenous Valve Assembly" to Peter Leslie Steer and Paul Hex Venn. This patent discloses devices for administering intravenous injections of liquids such as drugs, anesthetics or transfusion liquids. The device includes a valve body having a holder for an injection needle, with the holder provided with an outlet passage that communicates with the needle. A nonreturn valve is arranged in the valve body, and a valve operating plunger has a portion projecting from the body to enable the valve to be opened by operation of the plunger, which has an inlet passage through which liquid to be injected can pass from a syringe into the valve body and thence pass the nonreturn valve to the outlet passage.

Yet another slotted-disk device of undue complexity is in U.S. Pat. No. 3,848,579, issued Nov. 19, 1974 for "Automatic Elasto-Valvular Hypodermic Sampling Needle" to Antony-Euclid Villa-Real. This patent discloses a blood-drawing device with an automatically actuatable elastovalvular mechanism, sensitive to pressure differential changes, attaining variable aperture sizes in the opening phase aimed to reduce mechanical hemolysis of the red blood cells and other cellular disintegration caused by high shear forces, and, achieving a normally closed position to prevent blood drip. A valve is situated between a pair of pre-formed internal chambers that separate two axially arranged sharpened cannulas. A preferably transparent hub is provided for visual indication during extraction of singular as several separate fluid samples, such as venous blood, during a single venipuncture.

Another complex slotted-disk device is in U.S. Pat. No. 3,620,500, issued Nov. 16, 1971 for "Variable Aperture Fluid Flow Control Apparatus" to Louis S. Santomieri. This patent discloses controlling the rate of fluid flow through an intravenous infusion tube by varying the dilation of an opening in a diaphragm, and maintaining the dilation without constant attention, the dilation being controlled by the relative position of a male fitting with a female fitting.

A further complex slotted-disk device is in U.S. Pat. No. 3,601,151, issued Aug. 24, 1971 for "Nonreturn Valves for Medical Uses" to Ronald Winnard. Disclosed is a medical valve used to pass fluids into and from the body. The valve is constituted by a chamber into which a stem protrudes. The stem is provided with a bore which passes fluid into the chamber and through the valve, and acts as a seat for valve closure by an elastic-like sock which opens by expansion under pressure exerted from the stem. The valve is closed when the pressure is removed, and the sock contracts under its own elasticity around the stem. The valve can also be operated by a needle piercing the sock, which is self-sealing when the needle is removed.

Still another complex slotted-disk device is in U.S. Pat. No. 4,143,853, issued Mar. 13, 1979 for "Valve for Use With a Catheter or the Like" to Harvey J. Abramson. The disclosure is of a miniature valve for use with a catheter in which a cylindrical valve body has a male member and female member telescoped together to define opposed annular seats surrounding a through-opening. A disc of rubber having a central domed portion containing an axial slit is mounted between the seats, with the male and female members detented so that the periphery of the disc is pinched to displace rubber radially inwardly to keep the slit normally sealed against flow in either direction. The valve body has a female Luer connection adjacent the underside of the dome, and a male Luer connection adjacent the top of the dome. The female connection is spaced with respect to the disc so that when a cooperating Luer male connector is inserted into the female connection, the tip of the male connector engages the underside of the domed portion of the disc to open the slit and permit straight axial flow in either direction.

A further slotted-disk device of undue complexity is in U.S. Pat. No. 5,322,516, issued Jun. 21, 1994 for "Safety Needle System and Method For Using the Same" to James M. Brugger. A medical system is disclosed for transferring fluids (e.g. blood) to or from patients by a needle having a proximal end, a distal end attached to a syringe, a medial section, and an internal passageway. The medial section is elliptical in cross-section with dual arcuate side walls. The proximal end is blunt and rounded. Also included is an access site having a conduit with a resilient tubular port extending outwardly. The port includes a bore, and both the port and bore are elliptical in cross-section. A resilient compression member having an elliptical opening is positioned on a port to exert pressure and close the bore. In use, the needle is urged into the bore, temporarily deforming the compression member. After removing or delivering fluids using the syringe, the needle is withdrawn from the bore which is self-sealing by the compressive action.

A further slotted-disk device of undue complexity is in U.S. Pat. No. 5,322,518, issued Jun. 21, 1994 for "Valve Device for a Catheter" to Stefan Schneider, Kiel and Hans O. Maier. The disclosure is of a valve for a catheter with a hub. A tubular housing has one end with an outer cone for fitting into an inner cone of the catheter hub, and has an interior valve body acting as a locking member of an axial channel for the passage of an elongate object. The housing has an axially directed protrusion forming a radial space together with the outer surface of the outer cone. A locking member cooperates with a complementary member at the catheter hub, projecting into the space to act as a disconnection lock. The valve is for a catheter system for venous applications according to the Seldinger method, and provides sealing of the extracorporal end of the catheter.

Another complex slotted-disk device is in U.S. Pat. No. 5,322,517, issued Jun. 21, 1994 for "Disposable Automatic Hypodermic Needle Guard" to Richard C. Sircom, Yousel M. Youssef and Robert S. Solomon. Disclosed is a needle tip protecting device for hypodermic needles and catheters. The device is stored at the base of the needle prior to and during use. After use it can be slid to cover the needle tip where it automatically self-attaches and becomes non-removable.

Another slotted-disk device of complexity is in U.S. Pat. No. 4,778,453, issued Oct. 18, 1988 for "Medical Device" to George A. Lopez. Disclosed is a medical device used with a syringe that includes a needle protected by a guard. The needle has the end opposite its tip connected to the syringe. The guard is mounted on the needle and is movable axially along the shaft of the needle between a retracted position, enabling the needle to be inserted into a patient, and a forward position covering the tip of the needle. The guard is moved forward manually from the retracted to the forward position to protect against accidental needle sticks.

Another slotted-disk, complex device is in U.S. Pat. No. 5,322,515, issued Jun. 21, 1994 for "Luer Adapter Assembly for Emergency Syringe" to Peter J. Karas and Larry W. Pitts. The disclosure is of a Luer adapter assembly for a prefilled emergency syringe with a cylindrical sheath that extends coaxially with the syringe needle. The sheath can be integrally molded with the injector housing or attached to the syringe injector housing by spin welding or sonic welding. The sheath is joined to the housing so that an annual clearance space for the removable Luer adapter assembly is maintained between the tapered hub and the sheath. A removable cap on a threaded lock on the adapter extension is removed by twisting the cap in a first direction. The whole adapter assembly is removed from the tapered hub by twisting the cap is a second direction which is the same direction as the threads of the threaded lock.

Another complex, slotted-disk device is in U.S. Pat. No. 5,318,534, issued Jun. 7, 1994 for "Syringe for Balloon Catheterization" to Eli Williams and Evan Call. Disclosed is a syringe for inflation and rapid deflation of a balloon used in catheterization (transluminal angioplasty). The syringe has an actuated thread block engaged and disengaged by a rotary cam member interacting with the thread-engaging block. The block engages a threaded piston rod attached to the piston within the barrel of a balloon catheter syringe. A rotary cam engages the block to exert positive force on the block, either moving the block into a thread engaging or disengaging position. The syringe may also contain a segmented piston face so that a portion of the piston face is separately actuatable in order to introduce an increase in pressure while the main piston member remains stationary.

Other prior art which relates to connectors with elastomeric diaphragms having a central slit include Kennedy U.S. Pat. No. 962,027; Steer U.S. Pat. No. 3,570,484; Winnard U.S. Pat. No. 3,601,151; Santomieri U.S. Pat. No. 3,620,500; Villa-real U.S. Pat. No. 3,848,579 and Abramson U.S. Pat. No. 4,143,853.

Accordingly it is an object of the invention to facilitate the simplified control of fluid flow. A related object is to simplify the achievement of the "check valve" function in systems for intravenous and diagnostic therapy.

SUMMARY OF THE INVENTION

In accomplishing the foregoing and related objects, the invention provides a deformable elastomeric disk that is fixedly disposed between inlet and outlet members. The disk is deformable by pressure to permit flow through the inlet to the outlet, and a member is spaced from the disk for limiting the deformation thereof in the direction of pressure through said outlet to the disk.

In accordance with one aspect of the invention, the elastomeric disk is circular, positioned upon the outlet member and clamped between the inlet and outlet members.

In accordance with another aspect of the invention the disk has a slit therein to permit the desired deformation. The slit in the disk can be linear or nonlinear.

In accordance with a further aspect of the invention, the limiting member is integrated into the inlet member, and extends across the inlet member. The limiting member can be an apertured disk extending across the inlet member, and can be non-centrally apertured with a plurality of apertures that can be symmetrically and oppositely disposed.

The limiting member may have a pilot for facilitating the deformation of the disk, spanning the inlet member and extending short of the position where the disk is clamped.

A method of controlling fluid flow in accordance with the invention, may include (1) deforming an elastomeric disk fixedly disposed between inlet and outlet members to permit flow through the inlet member; and (2) limiting the deformation of the disk in the direction of pressure through the outlet member to the disk.

In accordance with one aspect of the method wherein the elastomeric disk is circular, positioned upon the outlet member and clamped between the inlet and outlet members, with a slit therein, the step of deforming the disk comprises expanding the slit. In the method wherein the limiting member is integrated into the inlet member, extends across the inlet member, the step of limiting deformation comprises restricting the motion of the disk by engaging the limiting member.

In the method of the invention wherein the limiting member comprises a non-centrally apertured disk extending across the inlet member, with a plurality of symmetrically and oppositely disposed apertures, a pilot is employed for facilitating the deformation of the disk.

DESCRIPTION OF THE DRAWINGS

Other aspects of the invention will become apparent after considering several illustrative embodiments, taken in conjunction with the drawings in which:

FIG. 1A is a plan view, to scale, of a flow control valve in accordance with the invention.

FIG. 1B is an enlarged cross-sectional view of the flow-control valve of FIG. 1A in its "check" condition;

FIG. 7B is a view of the flow control valve of FIG. 7A taken along the lines D—D;

FIG. 7C is a plan view of the slotted diaphragm included in the view of FIG. 7B;

FIG. 7D is a side view of the slotted diaphragm of FIG. 7C;

DETAILED DESCRIPTION

(a) First Embodiment of the Invention

Figure 2A:
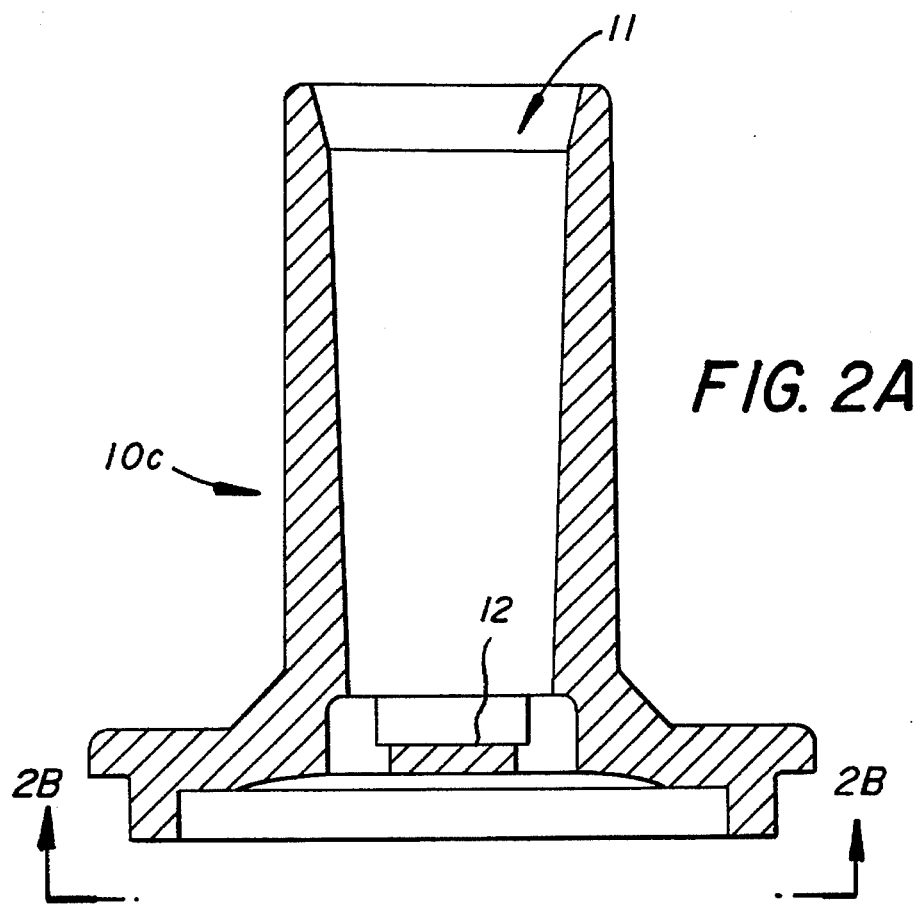
FIG. 2A is fragment of FIG. 1B illustrating details of the cap for the flow control device of FIG. 1A.

With reference to the drawings, a slotted-disk check valve 10 in accordance with the invention is shown to scale in FIG. 1A. As indicated in the enlarged cross-sectional view of FIG. 1B, the device 10 is formed by a base 10b and a cap 10c. The cap 10c contains an inlet flow channel 11, and the base has an outlet flow channel 22.

Figures 5A, 5B:
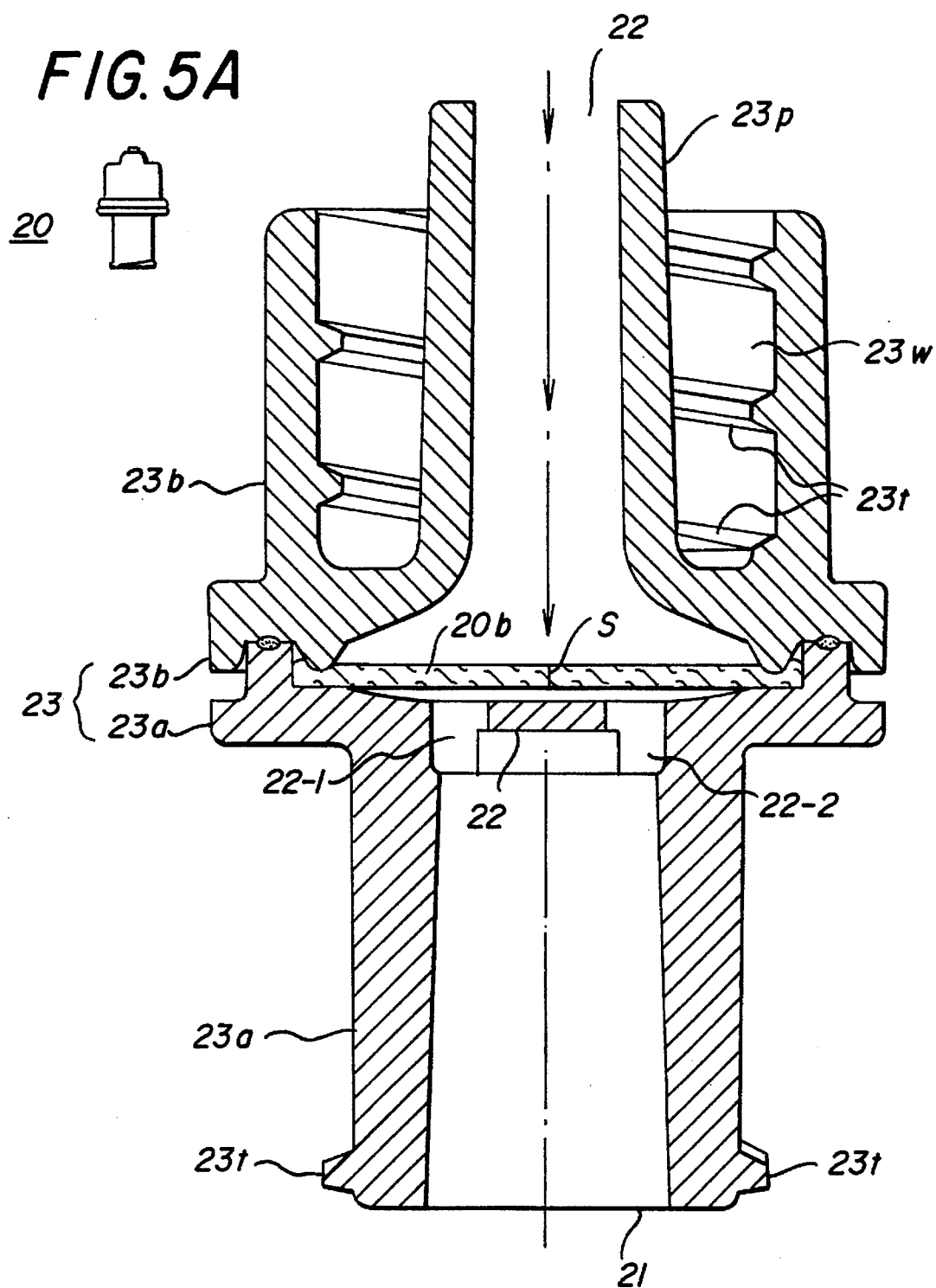
FIG. 5A is a plan view, to scale, of an alternative flow control valve in accordance with the invention.
FIG. 5B is an enlarged cross-sectional view of the alternative flow-control valve of FIG. 5A in its "check" condition.

Both the cap 10c and the base 10b are adapted to receive flow fittings, such as a tubing (not shown), but the valve 10 may be adapted as shown in FIGS. 5A and 5B for Luer fittings.

Figure 4:
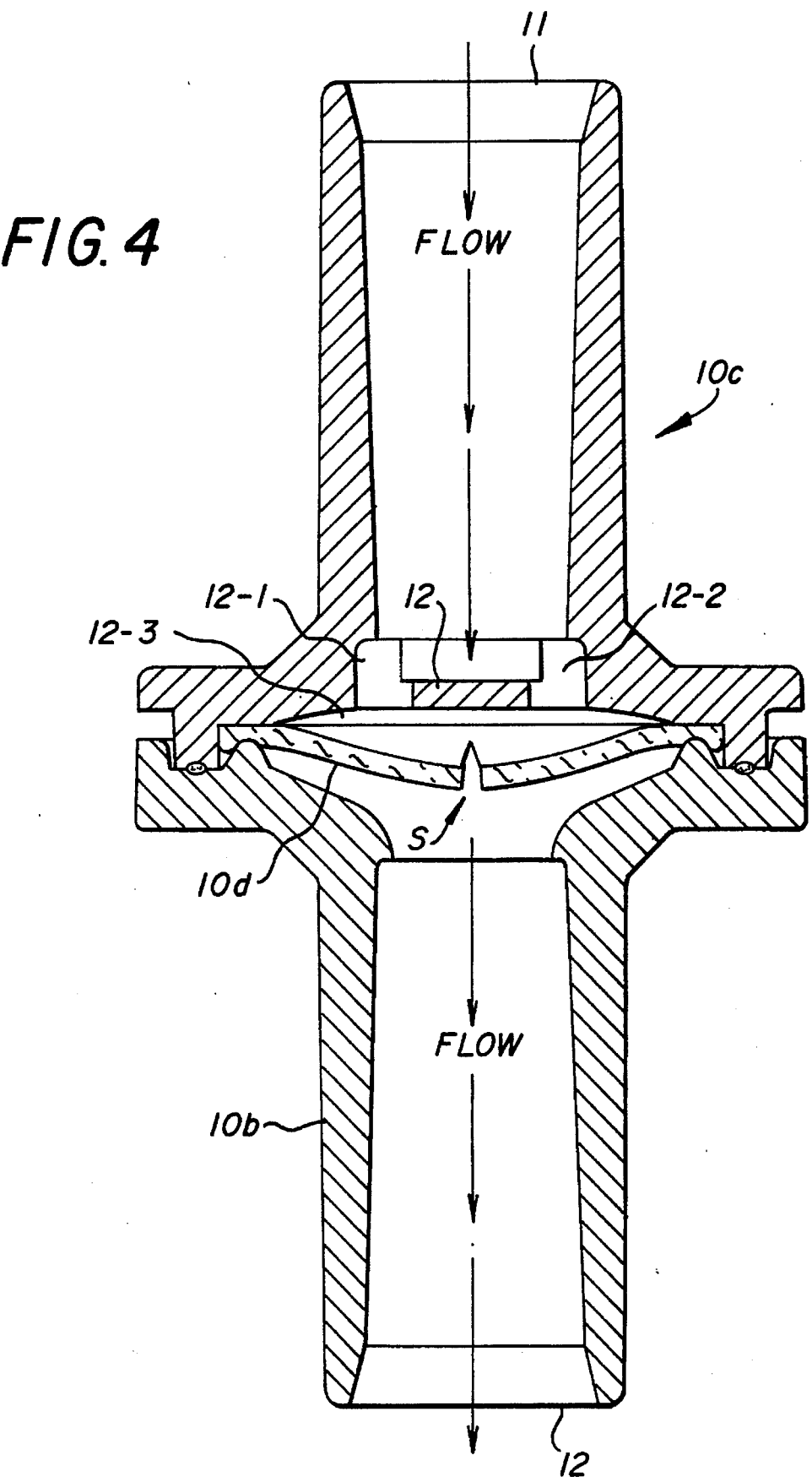
FIG. 4 is an enlarged cross-sectional view of the flow control valve of FIG. 1A in its "flow" condition.

Flow with respect to the channels 11 and 22 is selectively controlled in accordance with the operation of a control diaphragm or disk 10d that seals or "checks" the channel 11 when there is upward flow in the channel 22, and opens when there is downward flow in the channel 11, as shown in FIG. 4.

In the commonly provided check valve a diaphragm is unseated when there is downward flow. This creates a potential problem of diaphragm shift in operation, which is overcome by the invention since the disk 10d is tightly secured by being clamped between the cap 10c and the base 10b, and is of circular elastomeric material.

Figure 3A:
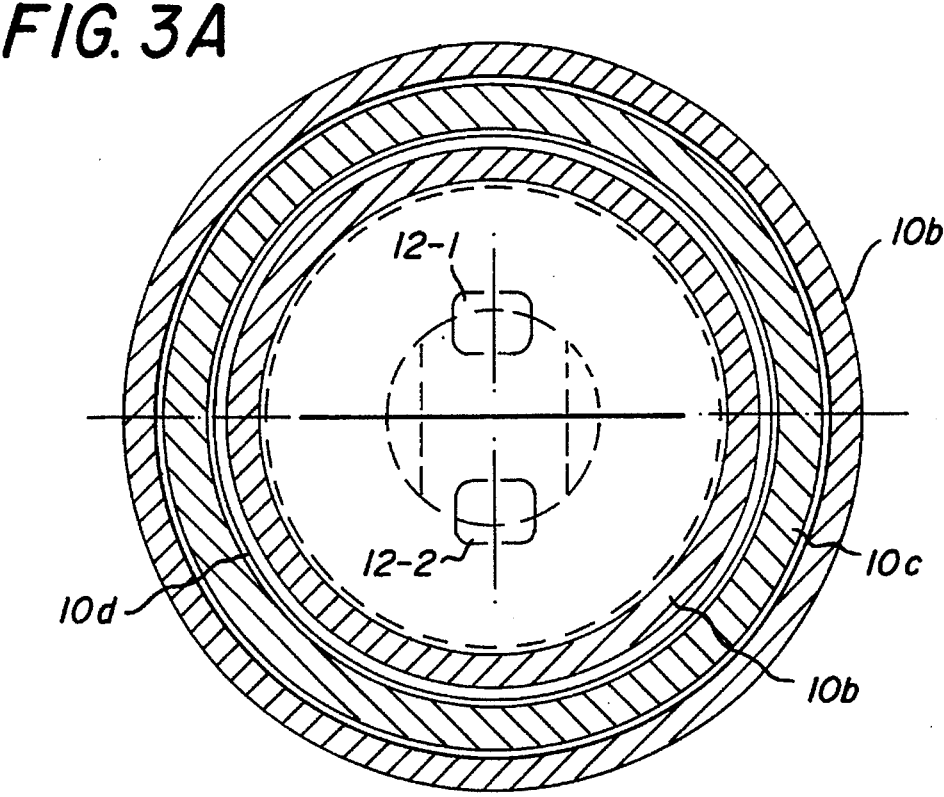
FIG. 3A is a view of the flow control valve of FIG. 1B taken along the lines A—A.
Figure 3B:
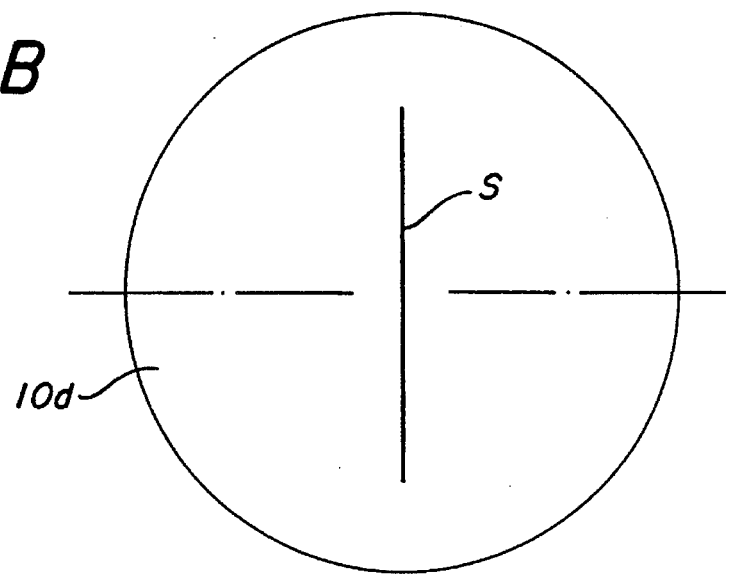
FIG. 3B is a plan view of the slotted diaphragm included in the view of FIG. 3A.
Figure 3C:
FIG. 3C is a side view of the slotted diaphragm of FIG. 3B.

Structurally the disc 10d has opposed surfaces and a central slit S as shown in FIG. 3B. In order to assure the "check" condition shown in FIG. 1B, the cap 10c has structure 12 spaced from the disk 10d for limiting the deformation thereof in the direction of pressure through the outlet 22 to the disk 10d.

In the particular embodiment of FIGS. 1B and 3B, the slit S in the disk 10d is linear, but the slit S may also be nonlinear. In either case the limiting structure 12 desirably is integrated into the cap 10c and extends across said inlet member.

Figure 2B:
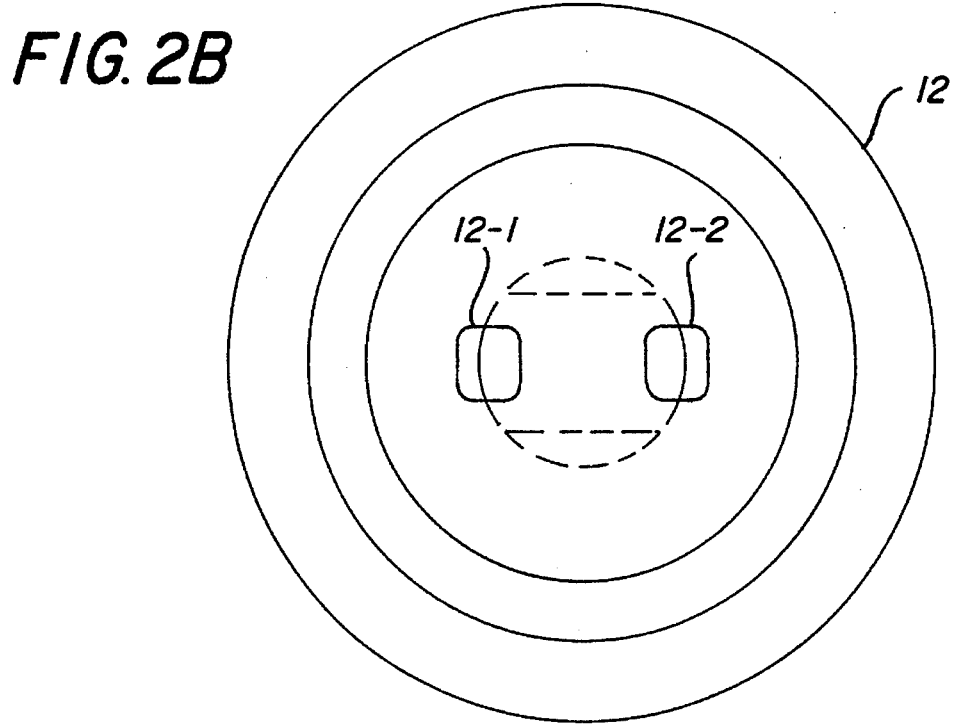
FIG. 2B is a view taken along the lines C—C of FIG. 2A.

As shown in FIG. 2B, the limiting structure 12 is an apertured disk extending across the inlet 11, and is non-centrally apertured with a plurality of illustrative openings 12-1 and 12-2 that are symmetrically and oppositely disposed.

In effect, the limiting structure 12 has a pilot 12-3 for facilitating the deformation of the disk 10d as shown in FIG. 4. The pilot 12-3 spans the inlet member 10c and extends short of the position where the disk is clamped.

The component elements of the device 20 are joined, for example, by ultrasonic welding. Upon assembly the diaphragm or disc 10d is securely held in position.

In the alternative flow control device 20 in accordance with the invention of FIG. 4 a housing 23 is again in two parts 23a and 23b. The part 23a includes an inlet 21 and a slotted flexible disc 20d, and a thread 23t specially designed to receive a Luer fitting of the kind incorporated into the part 23b. The body portion 23b has an inner wall 23w provided with threads 23t for attachment to a suitable flow structure. The central tubular portion constitutes an outer Luer taper 23p with an inner outlet opening 22.

FIG. 2A is fragment of FIG. 1B illustrating details of the cap for the flow control device of FIG. 1A.

Figure 2C:
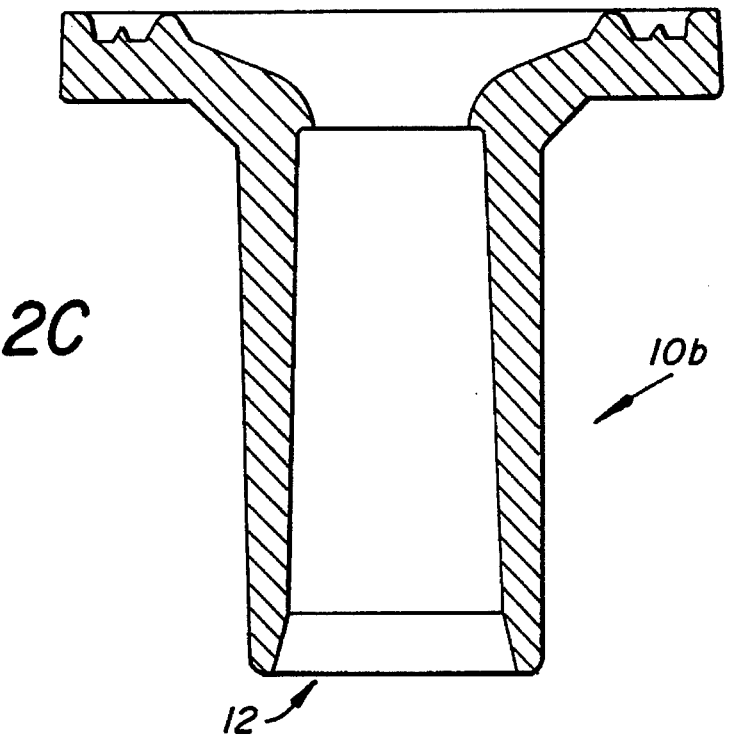
FIG. 2C is a fragment of FIG. 1B illustrating details of the base for the flow control device of FIG. 1A.

FIG. 2B is a view taken along the lines C—C of FIG. 2A;

The base for the flow control device of FIG. 1A is illustrated in detail in FIG. 2C, which is a fragment of FIG. 1B.

FIG. 5A is a plan view, to scale, of an alternative flow control valve in accordance with the invention, while FIG. 5B is an enlarged cross-sectional view of the alternative flow-control valve of FIG. 5A in its "check" condition.

Figure 6A:
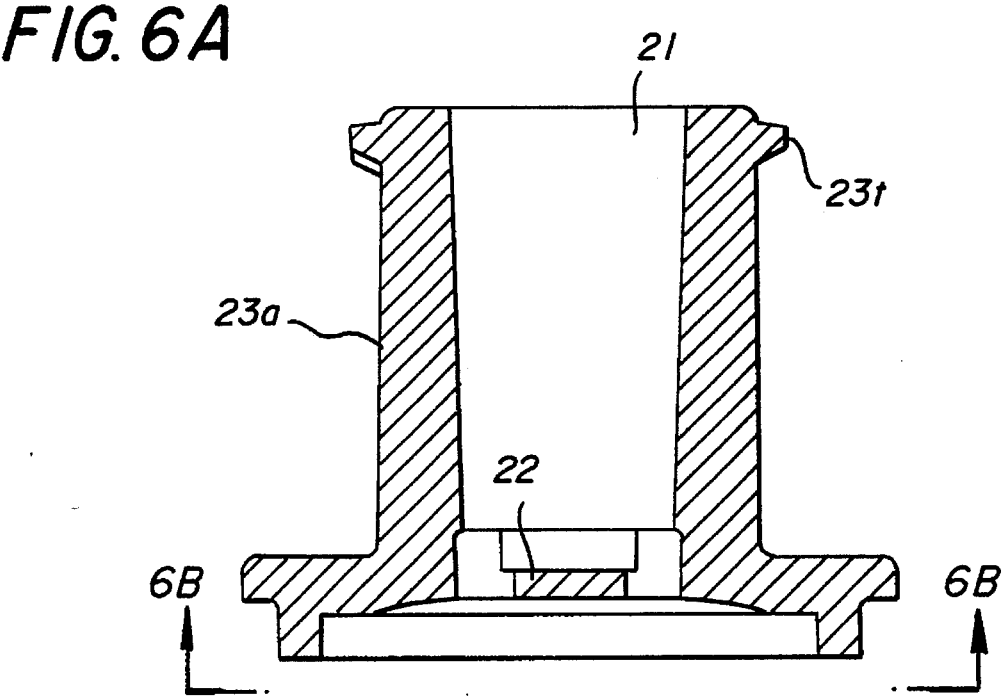
FIG. 6A is fragment of FIG. 5B illustrating details of the cap for the flow control device of FIG. 5A.
Figure 6C:
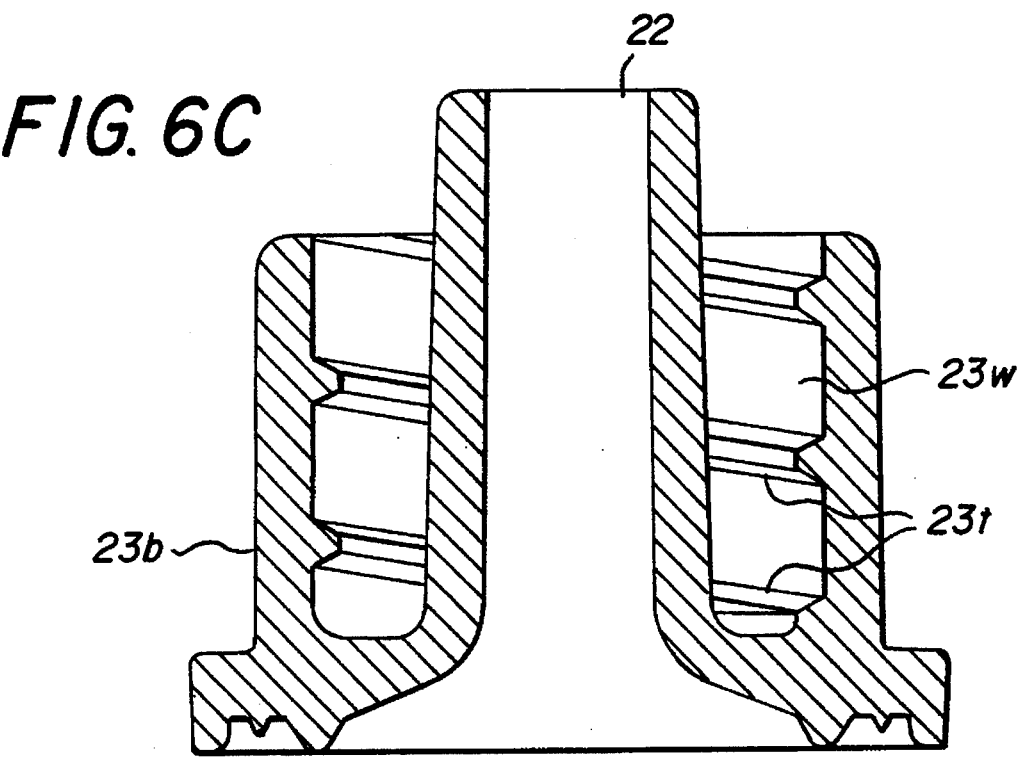
FIG. 6C is a fragment of FIG. 5B illustrating details of the base for the flow control device of FIG. 5A.
Figure 6B:
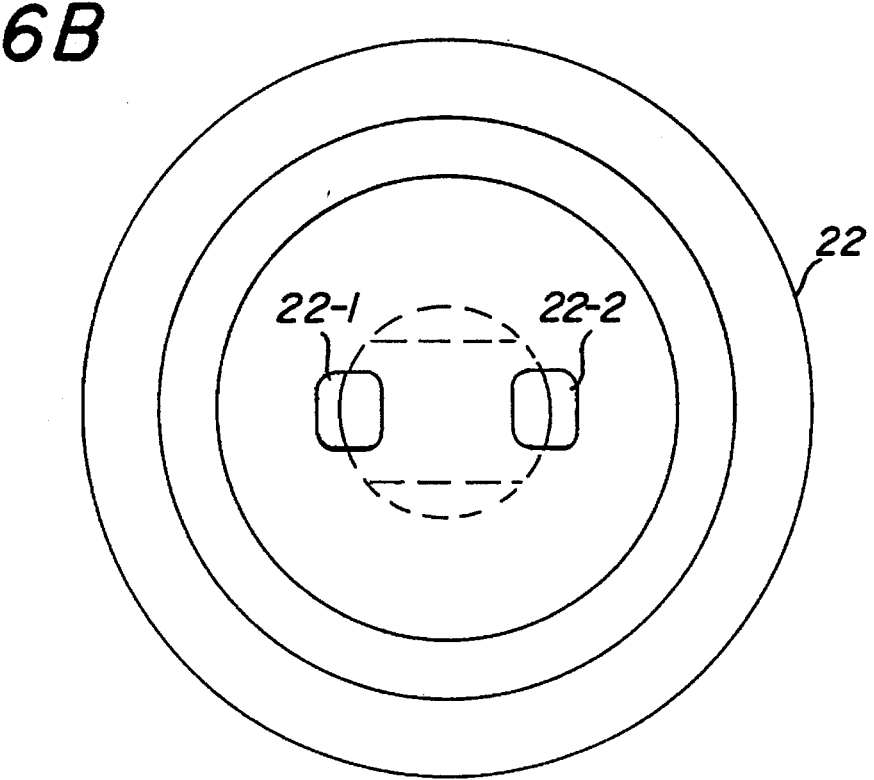
FIG. 6B is a view taken along the lines B—B of FIG. 6A.

FIG. 6A is fragment of FIG. 5B illustrating details of the cap for the flow control device of FIG. 5A, and FIG. 6B is a view taken along the lines B—B of FIG. 6A, with FIG. 6C being a fragment of FIG. 5B illustrating details of the base for the flow control device of FIG. 5A.

Figure 7A:
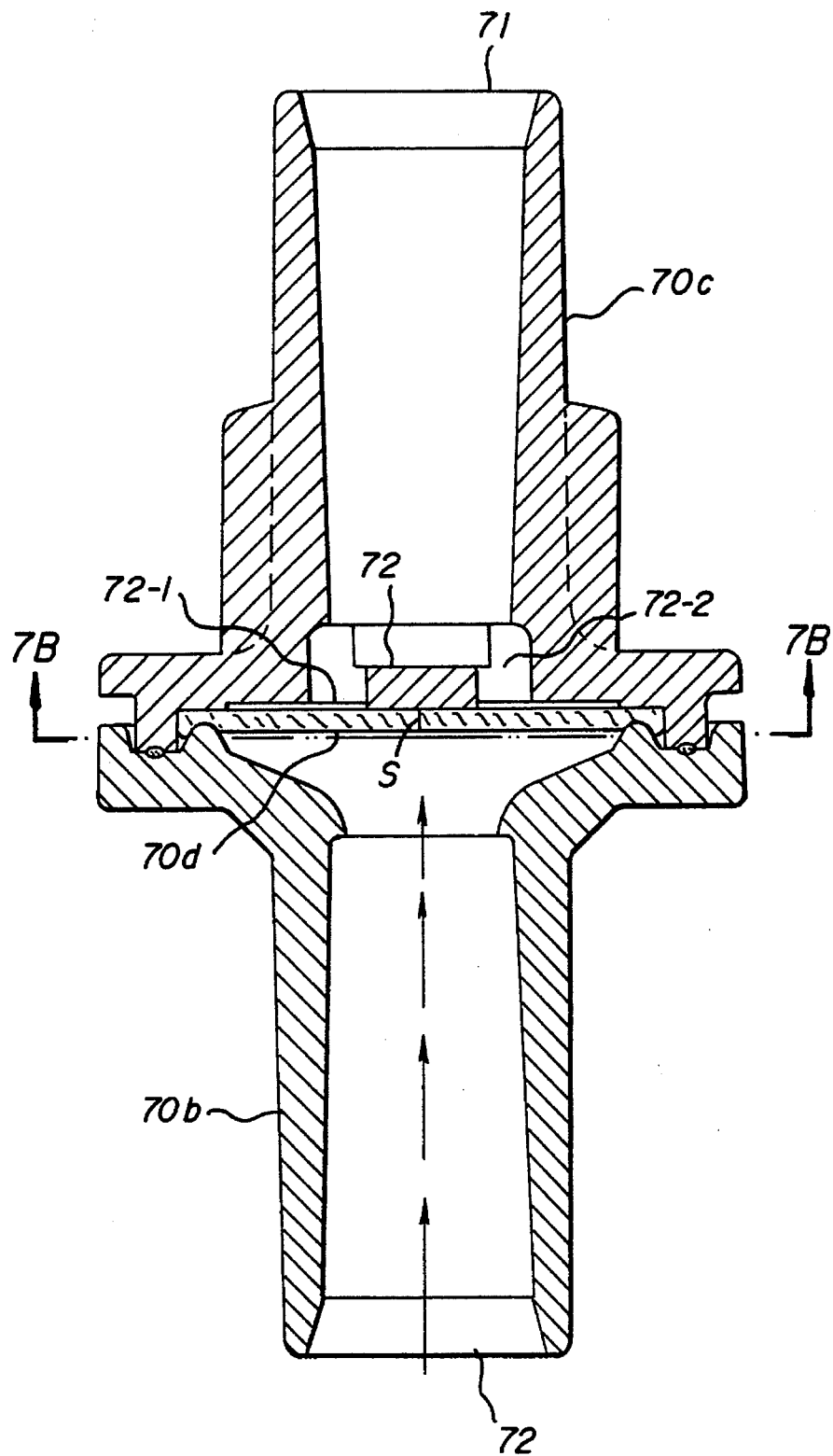
FIG. 7A is an enlarged cross-sectional view of a further alternative flow-control valve in its "check" condition.

FIG. 7A is an enlarged cross-sectional view of a further alternative flow-control valve in its "check" condition, and FIG. 7B is a view of the flow control valve of FIG. 7A taken along the lines D—D, with FIG. 7C being a plan view of the slotted diaphragm included in the view of FIG. 7B shown in side view in FIG. 7D.

Other aspects of the invention will be apparent to those of ordinary skills in the art.

What is claimed is:

1. Apparatus comprising an inlet member;

an outlet member physically connected to said inlet member;

an elastomeric disk fixedly disposed between the inlet and outlet members being deformable to permit flow through said inlet to said outlet; and means in said apparatus spaced from said disk for limiting the deformation thereof in the direction of pressure through said outlet to said disk and including a pilot for facilitating the deformation of said disk in the direction of pressure through said inlet.

2. Apparatus as defined in claim 1 wherein said elastomeric disk is circular.

3. Apparatus as defined in claim 1 wherein said disk is clamped between the inlet and outlet members.

4. Apparatus as defined in claim 1 wherein said disk is positioned upon said outlet member.

5. Apparatus as defined in claim 1 wherein said disk has a slit therein.

6. Apparatus as defined in claim 5 wherein said slit in said disk is linear.

7. Apparatus as defined in claim 5 wherein said slit in said disk is nonlinear.

8. Apparatus as defined in claim 1 wherein the limiting means is integrated into said inlet member.

9. Apparatus as defined in claim 1 wherein the limiting means extends across said inlet member.

10. Apparatus as defined in claim 9 wherein said limiting means comprises an apertured disk extending across said inlet member.

11. Apparatus as defined in claim 10 wherein said apertured disk is non-centrally apertured.

12. Apparatus as defined in claim 10 wherein said apertured disk has a plurality of apertures.

13. Apparatus as defined in claim 12 wherein said apertures are symmetrically disposed.

14. Apparatus as defined in claim 12 wherein said apertures are oppositely disposed.

15. Apparatus as defined in claim 1 wherein said pilot spans said inlet member and extends short of the position where the disk is clamped.

16. The method of controlling fluid flow, which comprises the steps of:

(1) deforming an elastomeric disk fixedly disposed between inlet and outlet members to permit flow through said inlet member and to said outlet member; and (2) limiting the deformation of said disk in the direction of pressure through said outlet member to said disk by a member, fixedly disposed between said inlet and outlet members, which facilitates the deformation of said disk in the direction of pressure through said inlet member to said disk.

17. The method of claim 16 wherein said elastomeric disk is circular, positioned upon said outlet member and clamped between the inlet and outlet members, with a slit therein, and the step of deforming said disk comprises expanding said slit.

18. The method of claim 16 wherein the limiting means is integrated into said inlet member, extends across said inlet member and the step of limiting said deformation comprises the step of restricting the motion of said disk by engaging said limiting means.

19. The method of claim 16 wherein said limiting means comprises a non-centrally apertured disk extending across said inlet member, with a plurality of symmetrically and oppositely disposed apertures, comprising a pilot for facilitating the deformation of said disk.

* * * * *